United States Patent
Kim et al.

(10) Patent No.: US 9,999,528 B2
(45) Date of Patent: Jun. 19, 2018

(54) STENT WITH EMBEDDED PRESSURE SENSORS

(71) Applicant: UNIVERSITY OF UTAH RESEARCH FOUNDATION, Salt Lake City, UT (US)

(72) Inventors: Hanseup Kim, Salt Lake City, UT (US); Ashrafuzzaman Bulbul, Salt Lake City, UT (US); Amit Patel, Salt Lake City, UT (US); Anwar Tandar, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 240 days.

(21) Appl. No.: 14/772,191

(22) PCT Filed: Mar. 13, 2014

(86) PCT No.: PCT/US2014/025580
§ 371 (c)(1),
(2) Date: Sep. 2, 2015

(87) PCT Pub. No.: WO2014/159991
PCT Pub. Date: Oct. 2, 2014

(65) Prior Publication Data
US 2016/0022447 A1    Jan. 28, 2016

Related U.S. Application Data

(60) Provisional application No. 61/784,104, filed on Mar. 14, 2013.

(51) Int. Cl.
*A61B 5/02*    (2006.01)
*A61F 2/86*    (2013.01)
(Continued)

(52) U.S. Cl.
CPC .............. *A61F 2/86* (2013.01); *A61B 5/0215* (2013.01); *A61B 5/02158* (2013.01);
(Continued)

(58) Field of Classification Search
CPC ...... A61F 2/86; A61F 2/82; A61F 2250/0002; A61F 2250/0096; A61F 2230/0069;
(Continued)

(56) References Cited

U.S. PATENT DOCUMENTS 4,380,932 A * 4/1983 Mott .................... G01L 9/0095
361/283.3
5,411,551 A    5/1995 Winston et al.
(Continued)

FOREIGN PATENT DOCUMENTS

| WO | 9829030 | 7/1998 |
|----|---------|--------|
| WO | 02098296 | 12/2002 |
| WO | 2008089282 | 7/2008 |

OTHER PUBLICATIONS

K. Takahata, Y. Gianchandani, and K. D. Wise. "Micromachined antenna stents and cuffs for monitoring Intraluminal pressure and flow" Journal of microelectromechanical systems, vol. 15, No. 5, (2006).
(Continued)

*Primary Examiner* — Navin Natnithithadha
*Assistant Examiner* — Eric Messersmith
(74) *Attorney, Agent, or Firm* — Michael Best & Friedrich LLP

(57) ABSTRACT

A stent including a wire tube and at least one pressure sensor in electrical contact with the wire tube. The pressure sensor includes a diaphragm in communication with a reservoir of liquid, a channel in fluid communication with the reservoir of liquid, and at least one pair of electrodes disposed on opposite sides of the channel, wherein deflection of the
(Continued)

diaphragm causes fluid to move from the reservoir into the channel.

23 Claims, 7 Drawing Sheets

(51) Int. Cl.
   *A61F 2/88* (2006.01)
   *A61B 5/0215* (2006.01)
   *A61B 5/00* (2006.01)
   *A61F 2/82* (2013.01)

(52) U.S. Cl.
   CPC ............ *A61B 5/4851* (2013.01); *A61B 5/686* (2013.01); *A61B 5/6862* (2013.01); *A61F 2/88* (2013.01); *A61B 2562/0247* (2013.01); *A61B 2562/043* (2013.01); *A61F 2/82* (2013.01); *A61F 2230/0069* (2013.01); *A61F 2250/0002* (2013.01); *A61F 2250/0096* (2013.01)

(58) Field of Classification Search
   CPC ........... A61F 2/88; A61B 5/00; A61B 5/0215; A61B 2562/0247; A61B 2562/043; A61B 5/02158; A61B 5/6862; A61B 5/4851; A61B 5/686
   See application file for complete search history.

(56) References Cited

U.S. PATENT DOCUMENTS

| | | | |
|---|---|---|---|
| 6,053,873 | A | 4/2000 | Govari et al. |
| 6,113,553 | A | 9/2000 | Chubbuck |
| 6,682,490 | B2 | 1/2004 | Roy et al. |
| 6,855,115 | B2 | 2/2005 | Fonseca et al. |
| 6,910,337 | B2 | 6/2005 | Flohr et al. |
| 6,910,377 | B1 | 6/2005 | Richter et al. |
| 7,147,604 | B1 | 12/2006 | Allen et al. |
| 7,452,334 | B2 | 11/2008 | Gianchandani et al. |
| 7,574,792 | B2 | 8/2009 | O'Brien et al. |
| 8,097,926 | B2 | 1/2012 | de Graff et al. |
| 8,212,552 | B2 | 7/2012 | Gianchandani et al. |
| 2002/0151816 | A1 | 10/2002 | Rich et al. |
| 2002/0183628 | A1* | 12/2002 | Reich ................. A61B 5/02014 600/486 |
| 2007/0028683 | A1* | 2/2007 | Ionescu-Zanetti ..... A61B 5/021 73/299 |
| 2012/0232460 | A1 | 9/2012 | Raven et al. |

OTHER PUBLICATIONS

K. Takahata, A. DeHennis, K. D. Wise, and Y. Gianchandani, "Stentenna: A micromachined antenna stent for wireless monitoring of implantable microsensors", Proceedings of the 25th annual international conference for the IEEE EMBS, Cancun, Mexico, (2003).
E. Y. Chow, Y. Ouyang, B. Beier, W. J. Chappell, and P. P. Irazoqui, "Evaluation of cardiovascular stents as antennas for implantable wireless applications", IEEE transaction on microwave theory and techniques, vol. 57, No. 10, (2009).
E. Y. Chow, A. L. Chlebowski, S. Chakraborty, W. J. Chappell, and P. P. Irazoqui, "Fully wireless implantable cardiovascular pressure monitor integrated with a medical stent" IEEE transaction on biomedical engineering, vol. 57, No. 6, (2010).
S. R. Green and Y. B. Gianchandani, "Wireless magnetoelastic monitoring of biliary stents", Journal of microelectromechanical systems, vol. 18, No. 1, (2009).
S. R. Green and Y. Gianchandani, "Wireless biliary stent system with wishbone-array resonant magnetoelastic (warm) sensor and conformal magnetic layer", . . . , vol. 1, No. 1, (2010).
N. M. Neihart and R. R. Harrison, "Micropower circuits for bidirectional wireless telemetry in neural recording applications", IEEE transaction on biomedical engineering, vol. 52, No. 11, (2005).
E. Park, J, Yoon, and E. Yoon, "Hermetically sealed inductor-capacitor (LC) resonator for remote pressure monitoring", Jpn. J. Appl. Phys., vol. 37, pp. 7124-7128, (1998).
P. S. Hall and Y. Hao, "Antennas and propagation for body-centric wireless communication", 2nd edition, (2012).
N. H. J. Pijls, N. De Bruyne, G. J. W. Bech, F. Liistro, G. R. Heyndrickx, H. J. R. M. Bonnier, and J. J. Koolen, "Coronary pressure measurement to assess the hemodyanamic significance of serial stenoses within one coronary artery: validation in humans", Circulation: Journal of the American heart association, vol. 102, pp. 2371-2377, (2000).
M. Soma, D. C. Galbraith, and R. L. White, "Radio-frequency coils in implantable devices: misalignment analysis and design procedure", IEEE transaction on biomedical engineering, vol. bme-34, No. 4, (1987).
F. W. Grover, "Inductance calculation", New York: Dover, (1973).
I. Ben-dor, R. Waksman, A. D. Pichard, J. Lindsay, and L. F. Satler, "The current role of bare-metal stents" Cardiac invention today, Cover story (2011).
S. Mohan, and A. Dhall, "A comperative study of restenosis rates in bare metal and drug eluting stents", International journal of angiology, vol. 19, No. 2, pp. 66-72, (2010).
J. Ritzema, I. C. Melton, A. M. Richards, I. G. Crozier, C. Frampton, R. N. Doughty, J. Whiting, S. Kar, N. Eigler, H. Krum, W. T. Abraham, and R. W. Troughton, "Direct left atrial pressure monitoring in ambulatory heart failure patients" Circulation, vol. 116, pp. 2952-2959, 2007.
Suter, Jonathan D. et al., "Principles of Meniscus Based MEMS Gas or Liquid Pressure Sensors," IEEE/ASME Journal of Microelectromechanical Systems (JMEMS), vol. 22, No. 3, pp. 670-677, 2013.
Kim, Hyun-Tae et al., "A Rapid Prototyped On-Chip Vacuum Gauge Utilizing the Volumetric Expansion of Trapped Air in a Sealed Microchamber," in the Proc. 15th Int. Conf. on Miniaturized Systems for Chemistry and Life Sciences (μTAS '11), Seattle, WA, Oct. 2-6, 2011, pp. 1119-1121.
PCT Search Report and Written Opinion for International Application No. PCT/US2014/025580 dated Aug. 4, 2014.
European Extended Search Report for EP Application No. 14772676.4 dated Aug. 2, 2016.

* cited by examiner

STENT WITH EMBEDDED PRESSURE SENSORS

CROSS REFERENCE TO RELATED APPLICATIONS

This application is a national stage filing under 35 U.S.C. 371 of International Application No. PCT/US2014/025580, filed Mar. 13, 2014, which, claims priority to U.S. Provisional Application No. 61/784,104, filed Mar. 14, 2013, which are incorporated herein by reference in their entireties.

BACKGROUND

The present invention relates to pressure-monitoring stents.

Stents are used in blood vessels to treat the obstruction of blood flow in the cardiovascular system. The use of stents has become a great tool for the treatment of the cardiovascular diseases. Stents include a flexible mesh-like hollow tube that can expand with the help of an angioplastic balloon, thus helping to improve blood flow in cases of occlusion due to plaque accumulation.

Though a stent helps to expand the narrowing effect of the arteries, it also frequently gets "re-covered" by plaque (restenosis) or endothelialization. Patients must be periodically monitored after stent implantation to check for restenosis. It has recently been reported in the literature that re-endothelialization typically takes place within 3-4 months after placing a bare metal stent and within 6 months for drug eluting stent. It has also been reported that 48.8% and 23.1% of the patients experienced restenosis for bare metal stents and drug eluting stents, respectively, from a total of 130 patients in the study. It is estimated that the size of the worldwide vascular stent market was approximately $8 billion in 2008 and $10.5 billion in 2010. Both clinically and economically, there exist great demands in developing an implantable stent that monitors the growth of intravascular tissues without invasive surgery.

Currently the most widely-used monitoring practice is to open a small incision on the patient's body into which a long wire-pressure sensor is inserted. The wire sensor reports pressure differences between two positions across the stent, which indicate the developmental stages of restenosis if any. Note that pressure will be accumulated or decreased respectively in front of or behind the narrowing portion of the vessel, creating a certain amount of pressure difference across the narrowed vessel part. In short, currently patients need to go through incision surgery-based tests every three months for restenosis monitoring.

In order to avoid such invasive procedure, which requires enormous medical costs, expertise, time, and may cause pain to the patient, it would be greatly desirable to develop a stent that can monitor plaque or restenosis development in situ in a non-invasive manner. One possibility is a stent that is capable of monitoring intravascular pressure.

A pressure-monitoring stent is required to provide three specific functions of (1) a mechanical structure to open up the narrowing vessel, (2) pressure monitoring to evaluate any risks of restenosis, and (3) wireless signal transfer from the pressure sensor inside a patient to the external electronic reader. Typically, each function is realized in respective components.

To date, several pressure-monitoring stents have been reported which can be categorized into 3-, 2-, and 1-component systems. While multiple (3 or 2) component systems have demonstrated successful in vivo testing in pigs, they still can impose significant difficulties and dangers during practical surgery, compared to the conventional stent, due to the excessive volume, stiffness, and handling difficulty stemming from the additional components. On the other hand, the 1-component systems provide essentially the same level of surgical risks and procedures as the conventional mechanical stent (i.e. which provides no pressure measurement), while enabling the monitoring of in situ pressure inside the stent. Thus, the 1-component system is clearly more advantageous.

A one-component pressure-monitoring stent system has been developed utilizing magnetoelastic sensors. By utilizing a magnetic material as the stent structure, the stent system, without containing discrete pressure sensors or circuits, is capable of monitoring the plaque deposition through magnetic vibration property changes. When the whole stent is vibrated by the external magnetic field, it produces shifts of the resonance frequency depending on the plaque deposition level that affects the stiffness and mass of the whole stent.

However, the magnetic-vibration-based stent inherently suffers a weak signal that can be easily buried under the mis-alignment or tilting of the monitoring readers and magnetic interference in the measurement environment. This stent also lacks precision, as it provides a lumped output from the whole stent section and does not report the pressure difference across the stent. Further, it does not allow multiple-zone monitoring within the stent interval.

Thus, further improvements in pressure-sensing stents are needed.

SUMMARY

Accordingly, the stent disclosed herein addresses the deficiencies of the stents discussed above and provides a solution for a 1-component, large signal-to-noise ratio, and high-precision and multiple-zone pressure-monitoring stent. The 1-component structure is realized by building a pressure sensor into the stent wire and utilizing the stent wire also as the signal radiation LC coupler and antenna; a large signal-to-noise ratio is achieved by the fluidic-amplification-based pressure sensor; a high-precision signal is achieved through multiple-electrode fluidic signal digitization; and multiple zone pressure-monitoring is enabled by building several pressure sensors into the wire. Additionally, this stent is capable of providing data that are sufficient to visualize the images of the in situ plaque development. It also enables the distinction of simple endothelialization (global in the stent) and restenosis (local blocking in the stent).

In one embodiment, the invention provides a stent including a wire tube and at least one pressure sensor in electrical contact with the wire tube. The pressure sensor includes a diaphragm in communication with a reservoir of liquid, a channel in fluid communication with the reservoir of liquid, and at least one pair of electrodes disposed on opposite sides of the channel, wherein deflection of the diaphragm causes fluid to move from the reservoir into the channel.

In another embodiment the invention provides a stent including a wire tube and at least one pressure sensor in electrical contact with the wire tube. The pressure sensor includes a diaphragm in communication with a reservoir of liquid, a channel in fluid communication with the reservoir of liquid, and a plurality of pairs of electrodes, each pair disposed on opposite sides of the channel, wherein deflection of the diaphragm causes fluid to move from the reservoir into the channel.

Other aspects of the invention will become apparent by consideration of the detailed description and accompanying drawings.

BRIEF DESCRIPTION OF THE DRAWINGS

FIG. 1(a) shows an overview and FIG. 1(b) shows a cross-sectional view.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
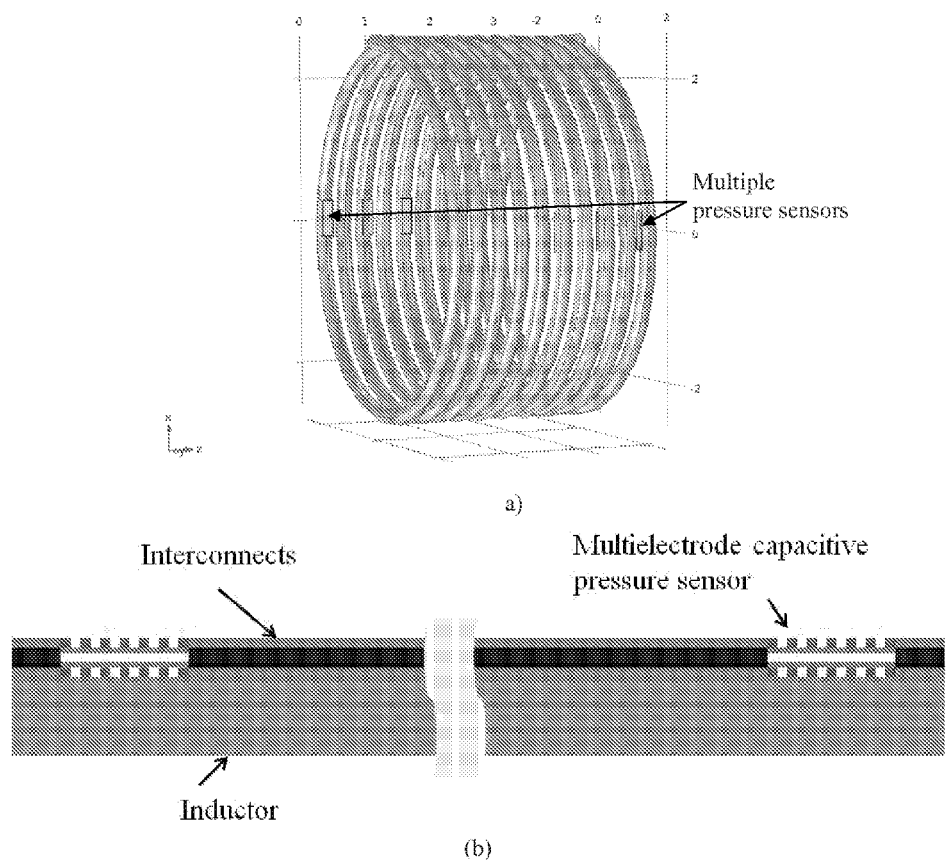
FIG. 1 shows a capacitive pressure sensor integrated stent.

Disclosed is a pressure-sensor-embedded-stent for performing in situ measurements of blood pressure inside a vessel and thus could provide advance notices of restenosis, a common failure mechanism for stents-implanted patients, ultimately obviating the periodic needs for invasive surgery simply to monitor the development of plaque deposition (FIG. 1). Various embodiments of the disclosed stent include one or more of the following features: (1) a minimally-profiled "on-wire" pressure sensor that is embedded in the stent to prevent any difficulties during insertion surgery, (2) a multiple-zone pressure sensor scheme to assist visualizing or profiling the in situ restenosis development status, (3) microfluidic-amplification of capacitance changes for higher signal resolutions against tiling or mis-alignment errors of inductive coils or physiological pressure drift, (4) fluidic-digitization of the capacitance variation to obviate of the needs for ASIC circuitry, (5) frequency-division recognition of multiple sensors, and (6) intrinsic battery-less and wireless approach. To enable non-invasive monitoring of restenosis, the stent is utilized as a wireless inductive power link and at the same time as an antenna to radiate the pressure information, as shown in FIG. 1.

Previously reported pressure-monitoring stents, e.g. those disclosed in the academic literature, exhibit practical difficulties when they are surgically implanted because they contain either discrete pressure sensor components that limit the minimum size and bending flexibility or discrete ASIC chips that require significant amounts of power. Among other difficulties, stents with discrete components impose challenges when they are inserted through arbitrarily-shaped vessels which might require bending of the stent. Additionally, the profile of the components may contribute to plaque accumulation by causing pressure gradients across the components. A one-component stent has been reported which utilizes the subtle stiffness/mass changes of the stent as the indication of restenosis; however, this design is intrinsically limited in accuracy due to the lack of multiple-zone measurement capability. Additionally, the output signal resolution is inherently low due to the small amount of changes from restenosis and its signal can be easily ambiguous during readout due to tilting or mis-aligned positions of the reading device.

Figure 9:
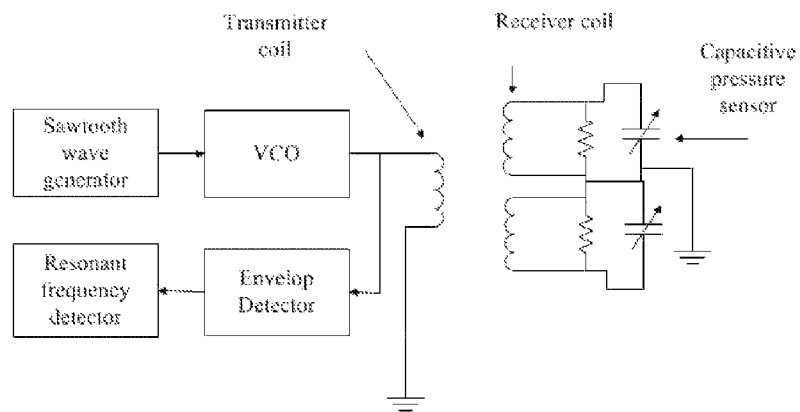
FIG. 9 shows a schematic diagram of the system.
Figure 10:
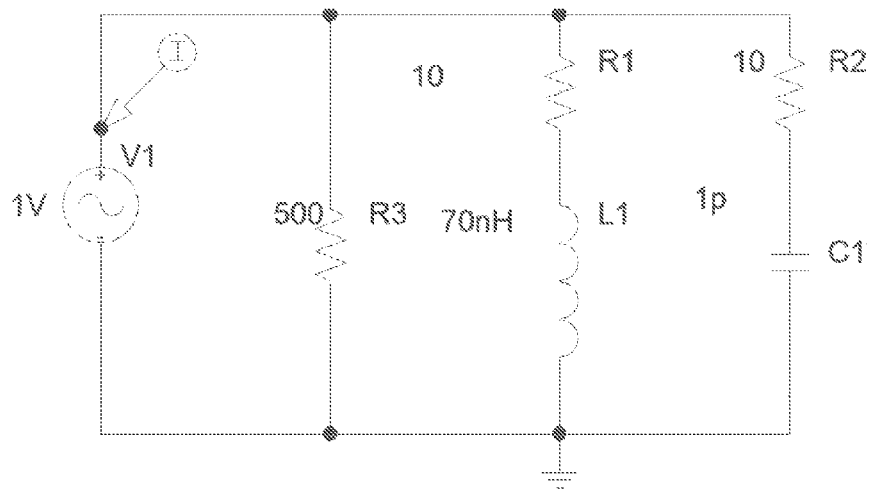
FIG. 10 shows an equivalent circuit diagram of the stent.

Accordingly, the disclosed stent includes the functions of a stent and a pressure sensor along with wireless communication capability, utilizing only a single-component structure. Embodiments of the disclosed stent include a pressure sensor-integrated stent where the pressure sensor acts as a capacitor and the stent coil behaves as an inductor for the resonance and simultaneously as an antenna to transmit the signal during resonance. FIG. 1(a) shows the structure of the sensor-embedded stent, where the capacitive pressure sensors are built onto a cavity created on the stent wire. The capacitors are connected through a low-resistance metal strip to the stent to form an LC tank, as shown in FIG. 1(b). FIG. 1(b) is a lengthwise cross-section through a section of stent wire showing that the pressure sensor embedded in the wire is flush with the outer surface of the wire. Since the inductor has some self-resistance, the whole structure forms a parallel resonance circuit as shown in FIG. 10. When pressure changes inside the blood vessels, the capacitance of the capacitive pressure sensor changes resulting in the shift of the resonance frequency in the resonance circuit. During resonance the signal radiates from the inductor (as an antenna) which can be detected by external tuning circuit located at the outside of the body as shown in FIG. 9.

The disclosed stent generates a signal with an improved signal-to-noise ratio compared to known stents. In this invention the capacitive pressure sensor amplifies the capacitance change by utilizing fluidic flows, as shown in FIGS. 4(a)-4(d), resulting in much larger capacitance changes under similar pressures compared to traditional capacitive pressure sensor.

The capacitive pressure sensor includes a diaphragm part and a fluidic channel part. FIG. 4(a) shows a first view of the stent, including a diaphragm coupled to a plurality of electrodes via a channel. FIG. 4(b) through 4(d) show a second view, perpendicular to the first, which depict the steps that occur when pressure increases in the vicinity of the stent. Pressure causes a deflection of the diaphragm, forcing fluid into the channel. As the fluid moves into the channel, the capacitance changes in a stepwise manner leading to automatic signal digitization, since there is an increase in capacitance each time the fluid moves between a pair of electrodes on opposite sides of the channel (e.g. compare FIG. 4(c) to FIG. 4(d)). Since the dielectric constant of many fluids including water is many times higher than the dielectric constant of air, there is a substantial stepwise increase in capacitance as the fluid level advances through the channel. Thus, development of plaques will increase pressure and deflect the diaphragm membrane downward, causing the working liquid under the diaphragm to flow out further in the fluidic channel. The channel contains several pairs of electrodes, each of which adds the corresponding capacitances to the total capacitance value. Since they are connected in parallel, their capacitance values will be simply added. Although water is used as the working media in many of the examples disclosed herein, in practice various fluids can be utilized as the working media for the pressure sensor.

Figure 4:
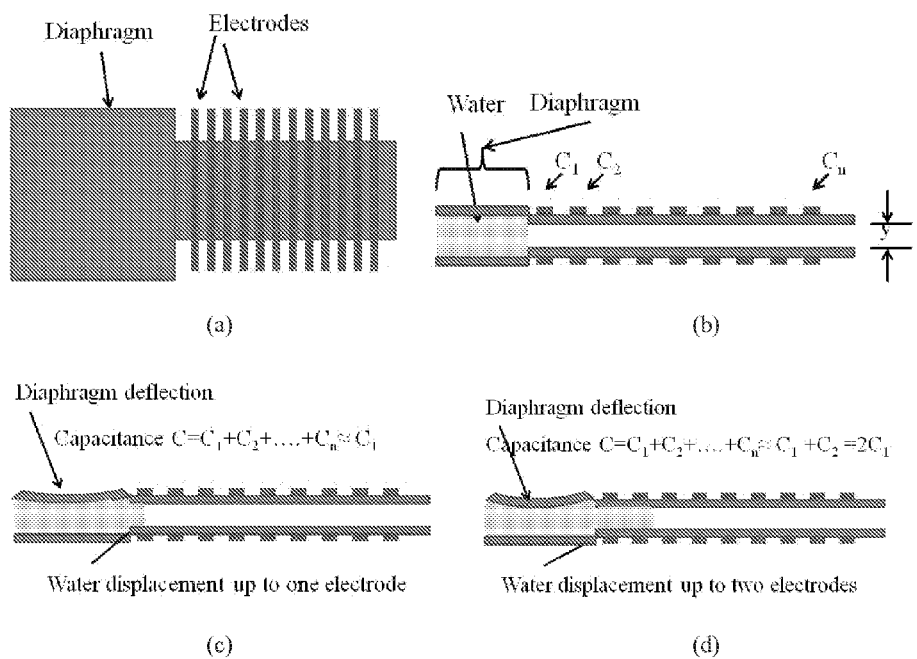
FIG. 4 shows a concept of providing digitization without any circuitry.

Note that the capacitance value, by the each pair of electrodes, is mainly determined by the existence of working fluid, following the equation below:

$$C = \varepsilon(\text{dielectric constant}) \frac{A(\text{Area})}{d(\text{gap})}$$

where a noticeable change can be made in the dielectric constant from 1 (air) to 80 (water, as an example) under the liquid fills the space between the pair of the electrodes. In this case, the capacitance of the electrodes filled with water is 80 times larger than that with air, thus dominantly contributing the total capacitance (FIG. 4). In other words, the number of pairs of electrodes that are filled with the working fluid flown by the diaphragm bending distinctively produces digitized capacitance value as shown in Table 1 below.

TABLE 1

| # of pairs filled with fluids | 1 | 2 | 3 | 4 | 5 | n |
|---|---|---|---|---|---|---|
| Total Capacitance | ~C | ~2C | ~3C | ~4C | ~5C | ~nC |

These resultant capacitance values are discrete, can be distinguished clearly, and fundamentally much larger (e.g. 80 times for water) than conventional capacitive pressure sensor values. Thus, they produce a larger signal-to-noise ratio that is beneficial against signal loss through wireless communication.

Note that by designing the diaphragm and the channel dimensions of width, length, depth, and thickness, the fluidic amplification ratio can be adjusted.

Figure 2:
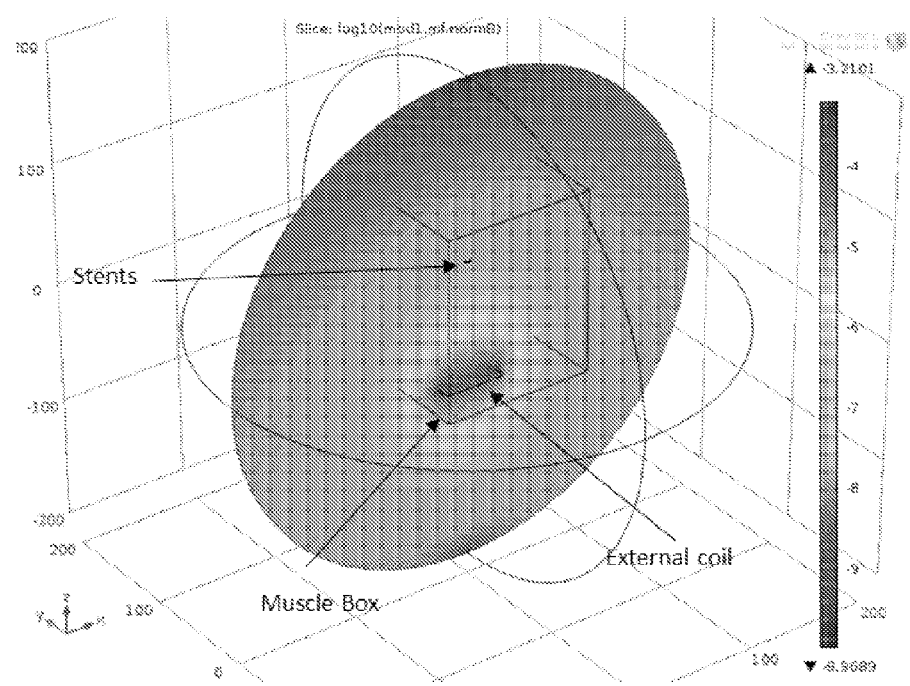
FIG. 2 shows an illustration of a simulation of inductive coupling from an external coil to an implanted stent.
Figure 3:
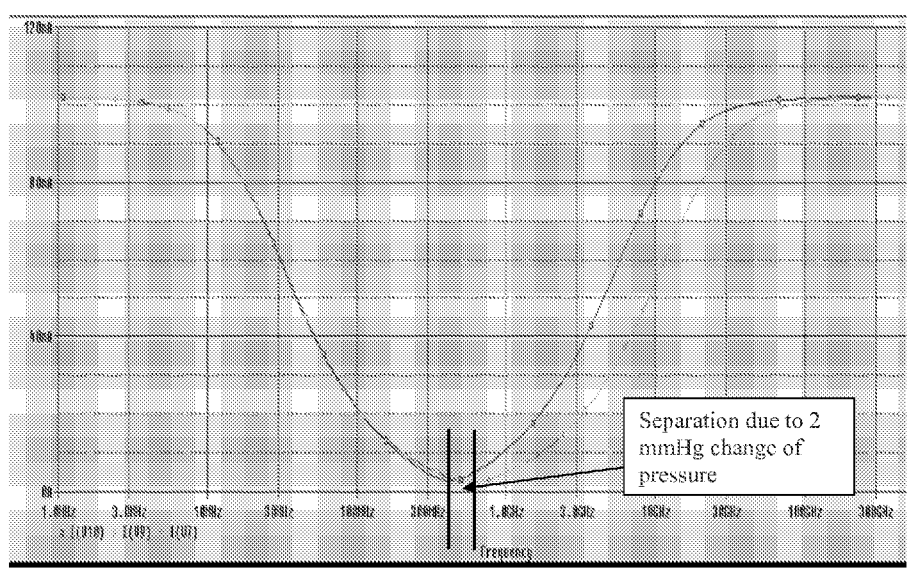
FIG. 3 shows predicted resonant frequency shifts due to tilting in the longitudinal and transverse directions using the model of FIG. 2.

Such amplification of the capacitance output from a pressure sensor also mitigates the potential errors due to tilting or misalignment. Inductive powering based on the coupling of magnetic fields generates mutual inductance in the stent inside the body. This mutual inductance varies due to the variation of angles against the primary coil outside the body. Such unwanted variation results in the shift of the resonance frequency for the measurement. However, due to the large signal output, it turns out that such variation becomes rather trivial using the presently-disclosed stent. FIG. 2 shows a simulation model designed to test the tilting effect over the mutual inductance. In this figure, the box simulates the body part, and inside the box two inductors (stents) are located. Each stent has the same coil-turns (3) and the same radius (5 mm). At the outside of the box, the primary coil is simulated as an external coil with a larger radius. Then this simulation monitored the variation of the mutual inductance between the two stents and the external coil while the external coil is rotated both in the longitudinal and transverse directions. The simulation results show that a 45° rotation in the longitudinal direction (i.e., if the external coil is rotated around the same plane of internal coils) changes the mutual inductance up to 0.2 nH and in the transverse direction up to 2 nH. These relatively small levels of change (<2 nH) correspond to signal changes that would occur for a pressure change of only 1 mmHg, which would correspond to a very thin layer of plaque deposition, as shown in FIG. 3. Thus, it is clear that the tilting up to 45° between the primary coil and the stent will not influence the pressure change measurement caused by the plaque deposition.

By using digitization (i.e. stepwise increases in capacitance due to pressure increases) of the output signal in combination of the signal amplification using the fluidic pressure sensor, the disclosed stent amplifies the minimum detectable signal, thus providing high precision. Digitization refers to dividing a range of data into some finite intervals and sending different signals for different intervals. Here, we divide the pressure range, as an example, 60~240 mm Hg into finite divisions and send different signals for different divisions, although other divisions of the pressure range are also possible.

The diagrams of FIG. 4 illustrate the process of digitization based on microfluidic amplification, a process which does not require any electrical circuitry. FIG. 4(a) shows the multi-electrode capacitor that includes a square diaphragm. Here water is used as a dielectric medium as an example. As described in the section above, for every pair of the electrodes that the working fluid reaches, the final capacitance is generally a multiple of the initial capacitance (nC).

The disclosed stent also enables a multiple-zone pressure monitoring as well as the visualization of the in-situ plaque development images. To monitor the pressure at different locations inside the blood vessels it is better to place a lot of pressure sensors at a number of locations on the stent. Moreover, such abundance provides fallback in the event of the failure of any one pressure sensor. With multiple sensors, multiple combinations among those sensors becomes enabled, where the such combinatory data sets produce data which can be used to predict the in situ location and surface profile of an endothelial growth or blocking by plaques across the stent, which may be extended to 3D profiles.

Figure 5:
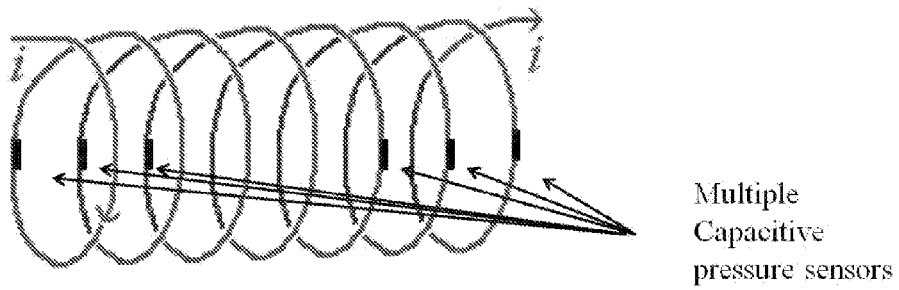
FIG. 5 shows a stent with multiple capacitive pressure sensors.

Each of the sensors has a particular resonant frequency that can be separated from the other sensors such that the external communication system can identify each sensor output, as shown in FIG. 5. In some embodiments, the stent may be made from multiple wires, each with a different resonant frequency and each having a separate group of sensors attached, such that a particular group of sensors can be separately addressed by providing an external signal with the appropriate frequency. In such embodiments, the wires, which are electrically insulated from one another, may each have a different length, thereby conferring a different resonant frequency, and each wire includes two sensors.

The resonance frequency of each sensor-wire set can be also varied by changing either the capacitance values of each sensor or inductance values of each wire. The nominal capacitance values of each sensor can be distinguished by varying the width, depth and shape of the fluidic channels or the width and length of the electrodes. The inductance values of each wire can be mainly decided by changing the lengths and diameters of the stent wires.

Endothelial cells may grow on the diaphragm of the pressure sensor after placing the stent inside the vessel. This phenomenon causes the following case problems as indicated in Table 2:

TABLE 2

| | No endothelial cells on the diaphragm | Endothelial cells on the diaphragm |
|---|---|---|
| No blocking/Narrowing of the blood vessel | Case I | Case III |
| Local blocking/Narrowing of the blood vessel | Case II | Case IV |

Figure 6:
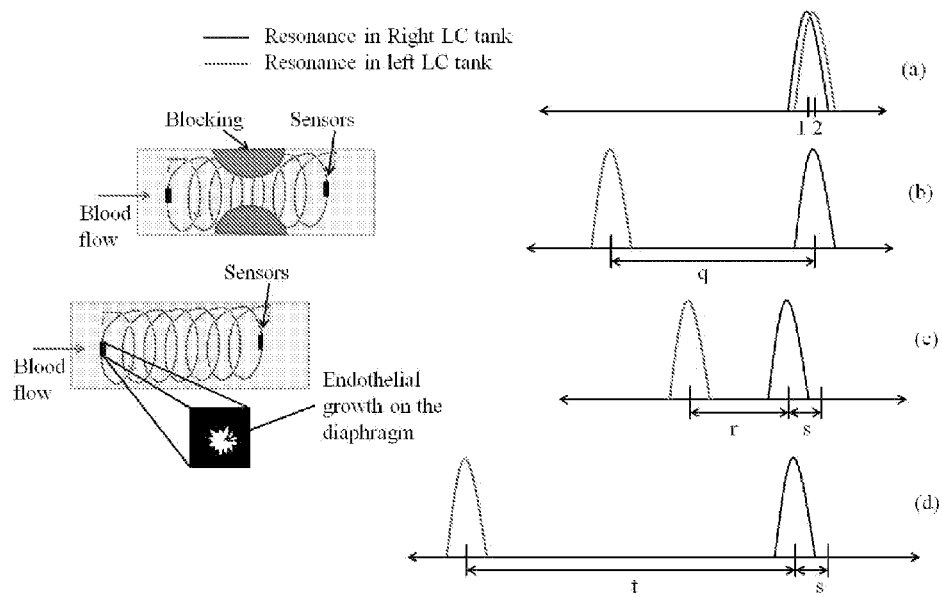
FIG. 6 shows a resonant frequency shift for different cases.

The device based on our idea will be able to differentiate among all of the cases which are described in FIG. 6. FIGS. 6(a), 6(b), 6(c), and 6(d) correspond to case I, II, III, and IV respectively. For case I, where there is no blocking and no endothelial growth on the diaphragm, both of the LC tanks will resonate at the same frequency since there is no pressure gradient. But the resonant frequencies may shift slightly due to some practical issues. For the next case (case II) which is shown in FIG. 6(b), due to blocking in the blood vessels there will be a pressure gradient and, in the illustrated example, the left side pressure will be higher than that of the right side. Therefore, the resonant frequency of the left LC tank will have a greater shift (q) than that of right side LC tank. In case III (FIG. 6(c)), it is shown that due to endothelial growth on both sensors, the resonant frequency of the right side LC tank will also shift(s). Since it is highly unlikely that the diaphragms of both sensors would accumulate the same amount of endothelial growth, therefore, there will still be a higher shift in the resonant frequencies (r) but this shift (r) will be much higher that of case I. Case IV is a combination of cases II and III, where the separation (t) is much greater than that of case II. The summary of detection of these four cases is given in Table 3.

TABLE 3

| | Case I | Case II | Case III | Case IV |
|---|---|---|---|---|
| Shift in the resonant frequencies | No shift | Very large shift but no or little change for right LC tank | Small shift and change for right LC tank | Very large shift and change for right LC tank |

To illustrate the operating principle, the design parameters in the examples disclosed herein have been chosen empirically. Nonetheless, in an implementation of the disclosed stent, selection and optimization of the parameters would be based on extensive research and measurement within the ability of one of skill in the art.

One such design parameter is resonant frequency. The frequency over which the disclosed stent can operate is in a range of about 200~700 MHz, which lies in the ISM band related with biomedical telemetry. For humans, the maximum range of blood pressure is about 60~180 mmHg. During sludge accumulation the pressure gradient for proximal stenosis is 42~0 mmHg and for distal stenosis the gradient is 45~−1 mmHg. Therefore, the ultimate pressure range is 59~225 mmHg, which can be approximated to 60~240 mmHg. Resolution of the pressure sensor can be set to 6 mmHg, although larger or smaller resolution values are also possible. For normal conditions when there is no narrowing or blocking of the blood vessels and for a minimum diastolic pressure of 60 mmHg, the resonant frequency may be 600 MHz, which is within the ISM band of RF telemetry. The inductance of a typical medical stent is about 100 nH. For simplification of the calculation we consider a solenoid-shaped inductor of the same inductance. From the formula of self-inductance of a solenoid:

$$L = \mu_0 \pi r^2 N^2 / l \quad (1)$$

Where L, r, N, l are the self-inductance, radius of the coil, turn ratio, and the length of the coil, respectively. For a typical stent radius r=2.5 mm, length l=3 cm. Since there are two LC tanks at the each end of the stent, there are two inductors of 50 nH each. From the COMSOL simulation result shown in FIG. 3, it was found that the mutual inductance is approximately 20 nH. From the parallel resonance equation shown below, the value of the capacitor is 1 pF for inductance of 70 nH (50 nH self+20 nH mutual) and resonant frequency of 600 MHz.

$$f = \frac{1}{2\pi\sqrt{LC}} \quad (2)$$

Previous researchers did not consider the misalignment (both lateral and angular) effect, which is very crucial in the frequency shift correlated pressure measurement. Since resonant frequency is inversely proportional to the square root of the inductance, a slight change in the mutual inductance will cause a large shift in the resonant frequency. The change in the mutual inductance due to both lateral and angular misalignment can be found from the following equation:

$$\frac{M_c}{M} = \sqrt{\frac{b}{(b+\Delta)\cos\alpha}} \frac{\left(\frac{2}{r}-r\right)K(r) - \frac{2}{r}E(r)}{\left(\frac{2}{k}-k\right)K(k) - \frac{2}{r}E(k)} \quad (3)$$

$$r = \sqrt{\frac{4a(b+\Delta)}{(a+b+\Delta)^2 + d^2}} \quad (4)$$

$$k = \sqrt{\frac{4ab}{(a+b)^2 + d^2}} \quad (5)$$

Where a, b, d, α, Δ, K( ), E( ) are radius of the primary coil, radius of the secondary coil, distance between the center of the two coils, angle of tilting, lateral misalignment, elliptic integral of the first kind, and elliptic integral of the second kind, respectively. For the aforementioned design parameters and considering primary coil (external coil) radius as a=30 mm, lateral misalignment as Δ=1 mm, angular misalignment as α=20°, the change in signal amounts to a 20% decrease in mutual inductance. For tilting of less than 25° the change in the mutual inductance is almost 2 nH which can be shown from equation (3). A simulation result obtained using COMSOL also reasonably proves this value.

The major effect is due to lateral misalignment. A 1 mm lateral misalignment causes about 20% decrease in mutual inductance and therefore a large shift in the resonant frequency. If we consider just the effect of angular misalignment, which causes a 2 nH change in the mutual inductance, the resultant shift in the resonant frequency is around 7~8 MHz. This happens without any pressure change hence causes ambiguity. Other researchers have identified a pressure response of 57.4 KHz/mmHg, which does not take into consideration the tilting effect. Since in the design of the presently-disclosed stent the capacitance changes as multiples of one capacitance unit (C), which in one embodiment is 1 pF, this creates a larger separation in resonant frequency shift. Given a blood pressure resolution of 6 mmHg and given that the dynamic range of the pressure gradient is 0~48 mmHg, the step size is 8. Thus, for every step i.e., for every 6 mmHg pressure change, water or other fluid under the diaphragm will move the water through the channel up to one electrode.

Figure 7:
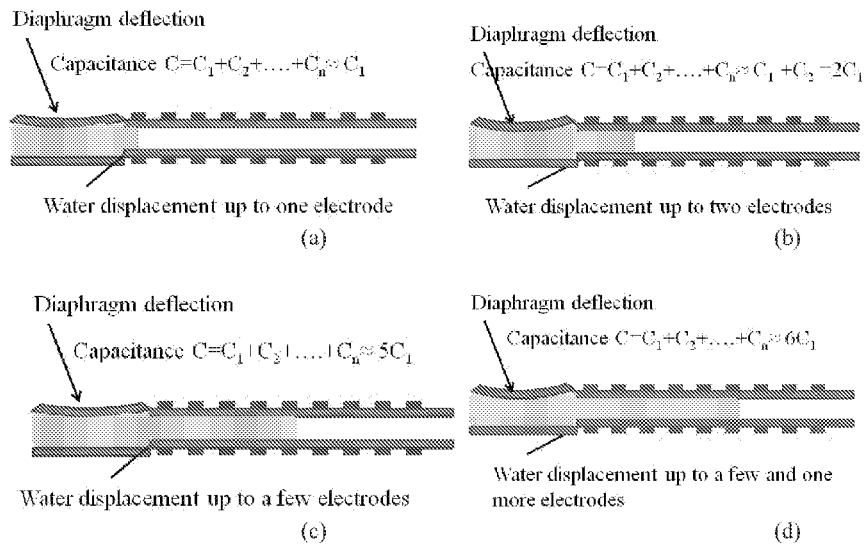
FIG. 7 shows fluid displacement due to pressure considering offset pressure.

The design overview of the multielectrode capacitive pressure sensor is shown in FIG. 2 and explained in detail in FIG. 7. In FIG. 7(a) the capacitance of one electrode is $C_1$=C=1 pF. When the pressure increases to the next step, which is 6 mmHg due to a narrowing effect, the water moves under two electrodes, and the total capacitance will be approximately $C_1+C_2$=2 pF (FIG. 7(b)). FIGS. 7(a) and 7(b) are for a minimum offset pressure of 60 mmHg and it is assumed that for this amount of minimum pressure water moves up to one electrode (FIG. 7(a)). If no blocking occurs (FIG. 7(a)) then both of the LC tanks have the same capacitance values and they will resonate at the same frequency. When blocking happens and pressure increases 6 mmHg due to blocking then capacitance gets doubled in one pressure sensor than that of the other and they will resonate at different frequency. FIGS. 7(c) and 7(d) are for another set of offset pressure, for example 90 mmHg, for which water moves up to 5 electrodes. If sludge accumulates then pressure increases more at one capacitive pressure sensor than the other, which will move water one more electrode than the other, i.e. the sensor in FIG. 7(d) experiences a higher pressure (6C) than the sensor in FIG. 7(c) (5C). As a result, the two sensors in FIGS. 7(c) and 7(d) will resonate at different frequencies.

Within the constraints of fabrication, the gap distance, y (see FIG. 4(b)), can be set at 3 μm, which makes the width of one electrode as:

$$C = \varepsilon A/y = \varepsilon lw/y$$

$$1 \times 10^{-12} = \frac{80 \times 8.854 \times 10^{-12} \times 150 \times 10^{-6} \times w}{3 \times 10^{-6}}$$

$$w = 28.2 \text{ μm}$$

Thirty electrodes are needed for thirty steps of resolution. The maximum capacitance will be $C_{max}$=30 pF which will create a resonance frequency at f=110 MHz. Therefore the inductor has to operate in the relatively large range of 110~600 MHz. However, since the primary or external inductor is tunable, this large range does not pose a problem. In those cases in which the inductor operates in a smaller range, there are other options. Since mutual inductance changes as much as 20% without alignment of mutual inductance, the capacitance can be changed by 50% for every step of resolution, whereas 100% of the capacitance change is used in the examples described above. Nevertheless, as long as the capacitance change due to one step of resolution is greater than that of the inductance change (due to misalignment), one can differentiate the shift in resonant frequency due to tilting (misalignment) from that due to actual blood pressure changes.

Figure 8:
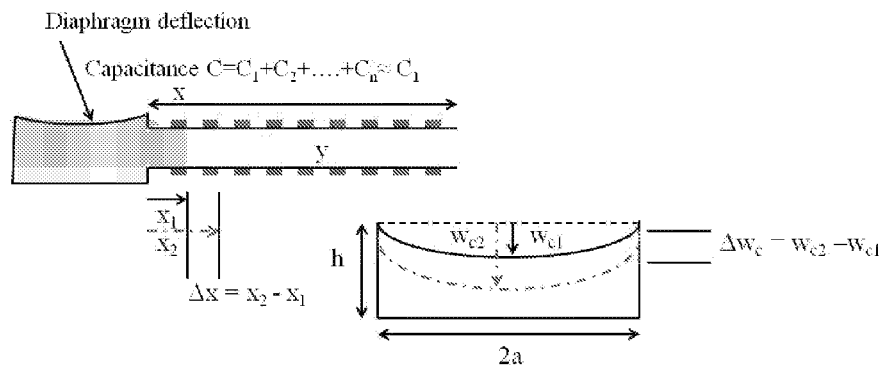
FIG. 8 shows a diaphragm design.

The diaphragm and the height or gap distance h of the diaphragm, as well as the dimensions of the channel, should be designed so that a 6 mmHg change in pressure leads to a deflection in the diaphragm that causes a linear displacement of one electrode, as explained below in FIG. 8. In FIG. 8 it is shown that volume reduction under the diaphragm, ΔV, which is equivalent to $\Delta w_c$ (center deflection) for a change in pressure of 6 mmHg, the lateral linear displacement should be Δx, which means ΔV=Δx*y*150 μm. To determine h, the height of the diaphragm chamber, the following relation is maintained: volume of the spherical cap formed by center deflection must be equal to the whole water channel, i.e., $$\Rightarrow V = \frac{\pi w_{c,max}}{6}(3a^2 + w_{c,max}^2) =$$

Each electrode width × total number of space and electrode × gap distance of each capacitor × length of each electrode $$\Rightarrow \frac{\pi w_{c,max}}{6}(3a^2 + w_{c,max}^2) = 28.2 \text{ μm} \times 60 \times 3 \text{ μm} \times 150 \text{ μm}$$

$$\Rightarrow w_{c,max} = 21.3 \text{ μm}$$

Assuming $w_{c,max}$=0.9*h, then the gap distance h under the diaphragm is approximately 24 μm (FIG. 8).

According to the equation of deflection of a square diaphragm as stated below, the amount of deflection is not linear with respect to applied pressure. The deflection vs. pressure curve gets saturated for higher pressure.

$$P = \frac{E}{1-v^2}\left(\frac{h}{a}\right)^4\left[4.20\frac{w_c}{h} + 1.58\left(\frac{w_c}{h}\right)^3\right] \tag{6}$$

where P, E, v, h, $w_c$, and 2a, are applied pressure, Young's modulus, Poisson's ratio, gap distance under the diaphragm, center deflection, and side length of the diaphragm, respectively. Since the relationship between deflection and applied pressure is not linear, therefore the electrodes at the far end (away from the diaphragm) need to be spaced more closely together, which is another design criteria.

FIG. 9 shows a diagram of a communication system for obtaining a reading from a stent such as those disclosed herein. The inductive power transfer occurs between the primary (labeled 'transmitter') and secondary (labeled 'receiver') coils when both sides resonate at the same frequency. Initially the primary coil transfers magnetic energy, hence inductive coupling occurs, but when the pressure changes in the capacitive pressure sensor, the resonant frequency of the secondary side is changed. The primary side then needs to be tuned to match the secondary side, which will change the impedance of the transmission coil. The equivalent circuit diagram is shown in FIG. 10, which shows a parallel resonance circuit.

Thus, the invention provides, among other things, a pressure-monitoring stent. Various features and advantages of the invention are set forth in the following claims.

What is claimed is:

1. A stent, comprising:
    a wire tube; and
    at least one pressure sensor in electrical contact with the wire tube, the pressure sensor including a diaphragm in communication with a reservoir of liquid, a channel in fluid communication with the reservoir of liquid, and a plurality of pairs of electrodes disposed on opposite sides of the channel, wherein deflection of the diaphragm causes fluid to move from the reservoir into the channel.

2. The stent of claim 1, wherein fluid moves into the channel between the at least one pair of electrodes.

3. The stent of claim 1, wherein each of the plurality of pairs of electrodes has a capacitance and wherein the capacitance increases when fluid moves into the channel between each of the plurality of pairs of electrodes.

4. The stent of claim 3, wherein the plurality of pairs of electrodes are connected in parallel.

5. The stent of claim 4, wherein the wire tube and the at least one pressure sensor form a circuit having a resonance and wherein the resonance changes when fluid moves into the channel between each of the plurality of pairs of electrodes.

6. The stent of claim 5, wherein the plurality of pairs of electrodes are spaced apart from one another and wherein the pairs of electrodes furthest from the diaphragm are spaced closer together than the pairs of electrodes closest to the diaphragm.

7. The stent of claim 1, wherein the wire tube comprises a plurality of wires that are electrically isolated from each other, wherein each of the plurality of wires has two pressure sensors in electric contact therewith.

8. The stent of claim 7, wherein each of the plurality of wires has a resonance that is different than a resonance of each of the other wires.

9. The stent of claim 1, wherein the at least one pressure sensor is embedded within a wire of the wire tube.

10. The stent of claim 1, further comprising a plurality of sensors, wherein the wire tube has a length and wherein the plurality of sensors are distributed along the length of the wire tube.

11. A stent, comprising:
 a wire tube; and
 at least one pressure sensor in electrical contact with the wire tube, the pressure sensor including a diaphragm in communication with a reservoir of liquid, a channel in fluid communication with the reservoir of liquid, and at least three pairs of electrodes, each pair disposed on opposite sides of the channel, wherein deflection of the diaphragm causes fluid to move from the reservoir into the channel.

12. The stent of claim 11, wherein fluid moves into the channel between at least one of the pairs of electrodes.

13. The stent of claim 12, wherein each of the plurality of pairs of electrodes has a capacitance and wherein the capacitance increases when fluid moves into the channel between each of the pairs of electrodes.

14. The stent of claim 13, wherein the pairs of electrodes are connected in parallel.

15. The stent of claim 14, wherein the wire tube and the at least one pressure sensor form a circuit having a resonance and wherein the resonance changes when fluid moves into the channel between each of the pairs of electrodes.

16. The stent of claim 11, wherein the pairs of electrodes are spaced apart from one another and wherein the pairs of electrodes furthest from the diaphragm are spaced closer together than the pairs of electrodes closest to the diaphragm.

17. The stent of claim 11, wherein the wire tube comprises a plurality of wires that are electrically isolated from each other, wherein each of the plurality of wires has two pressure sensors in electric contact therewith.

18. The stent of claim 17, wherein each of the plurality of wires has a resonance that is different than a resonance of each of the other wires.

19. The stent of claim 11, wherein the at least one pressure sensor is embedded within a wire of the wire tube.

20. The stent of claim 11, further comprising a plurality of sensors, wherein the wire tube has a length and wherein the plurality of sensors are distributed along the length of the wire tube.

21. A stent, comprising:
 a wire tube comprising at least one wire; and
 at least one pressure sensor embedded in the wire of the wire tube, each pressure sensor comprising a diaphragm in communication with a reservoir of liquid, a channel in fluid communication with the reservoir of liquid, and a plurality of pairs of electrodes disposed on opposite sides of the channel, wherein deflection of the diaphragm causes fluid to move from the reservoir into the channel.

22. The stent of claim 21, further comprising a plurality of pressure sensors embedded in the wire of the wire tube.

23. The stent of claim 22, wherein the wire tube comprises a plurality of wires, wherein each of the wire comprises a plurality of pressure sensors embedded therein.

\* \* \* \* \*